US006964694B2

(12) United States Patent
Rauchfuss et al.

(10) Patent No.: US 6,964,694 B2
(45) Date of Patent: Nov. 15, 2005

(54) DIESEL PARTICULATE FILTER MONITORING USING ACOUSTIC SENSING

(75) Inventors: Mark S. Rauchfuss, Scottsdale, AZ (US); Stephen R. W. Cooper, Fowlerville, MI (US); Nicholas M. Zayan, Fenton, MI (US)

(73) Assignee: AVL North America Inc., Plymouth, MI (US)

( * ) Notice: Subject to any disclaimer, the term of this patent is extended or adjusted under 35 U.S.C. 154(b) by 215 days.

(21) Appl. No.: 10/425,561

(22) Filed: Apr. 29, 2003

(65) Prior Publication Data

US 2004/0031386 A1 Feb. 19, 2004

Related U.S. Application Data

(60) Provisional application No. 60/376,380, filed on Apr. 29, 2002.

(51) Int. Cl.[7] .............................................. B01D 46/42
(52) U.S. Cl. ................. 95/1; 95/273; 96/417; 55/385.3; 55/523; 55/DIG. 30; 60/311; 73/38; 73/40; 73/40.5 A; 73/49.7
(58) Field of Search .............................. 95/1, 14, 273; 95/278; 96/383, 417, 420, 422; 55/385.3, 523, DIG. 30; 60/311; 73/38, 40, 40.5 A, 40.5 R, 49.7, 587

(56) References Cited

U.S. PATENT DOCUMENTS 4,064,962 A  * 12/1977  Hunt ........................ 181/272
5,497,099 A  *  3/1996  Walton ...................... 324/641
5,831,223 A  * 11/1998  Kesselring ................. 181/227
6,637,267 B2 * 10/2003  Fiebelkorn et al. ........... 73/587
6,666,070 B1 * 12/2003  Hagg et al. .................. 73/38

FOREIGN PATENT DOCUMENTS

| DE | 102 42 300 A1 | * | 3/2004 | ........... B01D/46/42 |
| JP | 7-102941 | * | 4/1995 | ............. F01N/3/02 |
| JP | 7-310525 | * | 11/1995 | ............. F01N/3/02 |
| JP | 8-121150 | * | 5/1996 | ............. F01N/3/18 |

* cited by examiner

Primary Examiner—Duane Smith
Assistant Examiner—Jason M. Greene
(74) Attorney, Agent, or Firm—Carlson, Gaskey & Olds, PC

(57) ABSTRACT

A particulate filter system is provided including an exhaust system transporting emissions from an engine. A filter such as a diesel particulate filter is disposed in the exhaust system. An acoustic sensor is associated with the exhaust system for detecting one or more frequencies passing through the filter. The frequency corresponds to a filter state indicative of a clean, full, loading, or failed filter. One or more acoustic sensors may fluidly or mechanically coupled to portions of the exhaust system to determine the frequency caused by the exhaust flow through the filter. The acoustic emissions from the filter may be used to compare to a known filter state to determine the present filter state. Alternatively, more sophisticated mathematical approaches may be used in which processed filter information is compared to a known filter state to determine the present filter state.

15 Claims, 2 Drawing Sheets

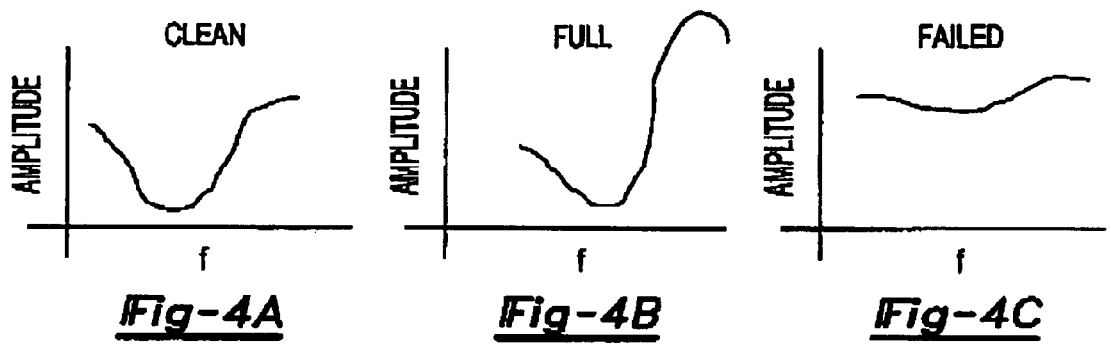
Fig-4A     Fig-4B     Fig-4C
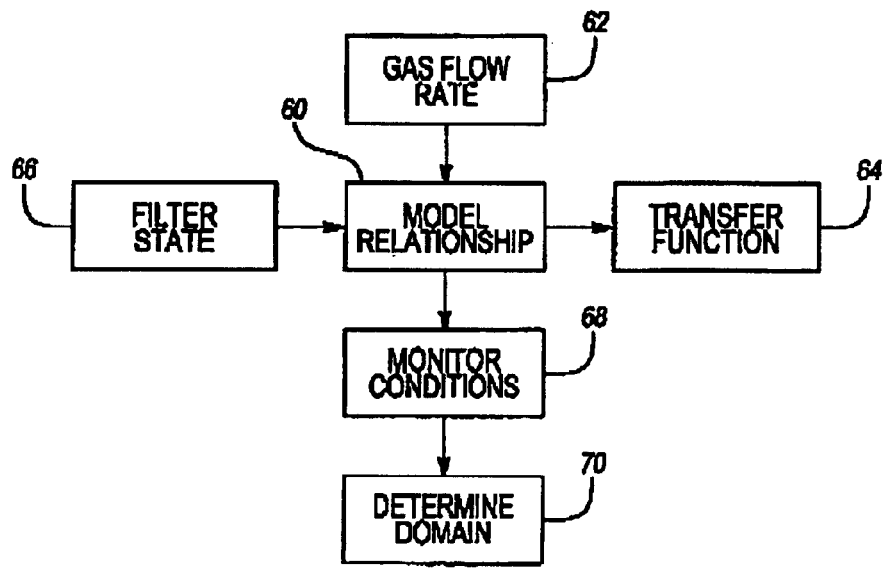
Fig-5

DIESEL PARTICULATE FILTER MONITORING USING ACOUSTIC SENSING

This application claims priority to Provisional Application Ser. No. 60/376,380, filed Apr. 29, 2002.

BACKGROUND OF THE INVENTION

This invention relates to a method and apparatus of monitoring the soot level in a diesel particulate filter.

Diesel engines employed in commercial vehicles typically have filters arranged in the exhaust system to filter particulate matter from the exhaust to comply with emissions standards. The filter may be used numerous times after it has become saturated before a new filter must be installed. There is a need to measure the level of soot loading in diesel particulate filters (DPF) for determining when it is time to perform a filter regeneration cycle in which soot is removed from the filter when it has become too clogged. There is also a need to determine if the filter is incapable of performing adequately such that regeneration may not be successfully performed due to a failure (breakdown, burn-through, etc.) of the substrate.

Present methodology for determining a filter's state is to measure the pressure drop across the filter. The pressure drop across a filter increases as the filter load increases. At some pre-determined pressure drop, the filter is run through a regeneration cycle. This methodology has drawbacks. The rate of filter loading influences the pressure drop behavior such that the filter may appear to be in need of regeneration later or sooner than necessary. Also, a breakdown or burn-through of the substrate leads to a low pressure drop "bypass" mode, which may be interpreted as a clean filter and would result in a significant blow-by and loss of filtering capability. Therefore, a more reliable method and apparatus are needed to determine the state of the DPF.

SUMMARY OF THE INVENTION AND ADVANTAGES

The present invention provides a particulate filter system including an exhaust system transporting emissions from an engine. A filter such as a diesel particulate filter is disposed in the exhaust system. An acoustic sensor is associated with the exhaust system for detecting a preselected frequency, frequencies or ranges of the acoustic spectrum (including infra and ultrasound) passing through the filter. The selected frequency, frequencies or frequency ranges correspond to a filter state indicative of a clean, full, loading, or failed filter. One or more acoustic sensors may be fluidly or mechanically coupled to portions of the exhaust system to determine the effect on the measured frequencies caused by the exhaust flow through the filter. The acoustic emissions through or from the filter may be used to compare to a known filter state to determine the present filter state. Alternatively, a more sophisticated mathematical approach may be used in which the acoustical transfer function is determined and the frequency resulting therefrom is compared to a known filter state or the determined transfer function is compared to one or more reference transfer functions characteristic of various preselected filter states such as loading, full, empty or failed.

Accordingly, the above invention provides a more reliable method and apparatus for determining the state of the diesel particulate filter.

BRIEF DESCRIPTION OF THE DRAWINGS

Other advantages of the present invention can be understood by reference to the following detailed description when considered in connection with the accompanying drawings wherein:

FIG. 4A is a graph of a clean filter;

FIG. 4B is a graph of a full filter;

FIG. 4C is a graph of a failed filter; and

FIG. 5 is a block diagram of the present invention filter monitoring system.

DETAILED DESCRIPTION OF THE PREFERRED EMBODIMENT

The present invention provides a method and apparatus to monitor the DPF soot loading and substrate failure. Several sensors may be used to monitor the DPF. A combination of pressure, temperature, and acoustical sensors may be used both upstream and downstream of the DPF to monitor its physical state. Additional information from the engine/exhaust controller may be used to quantify the exhaust flowing through the DPF.

Figure 1:
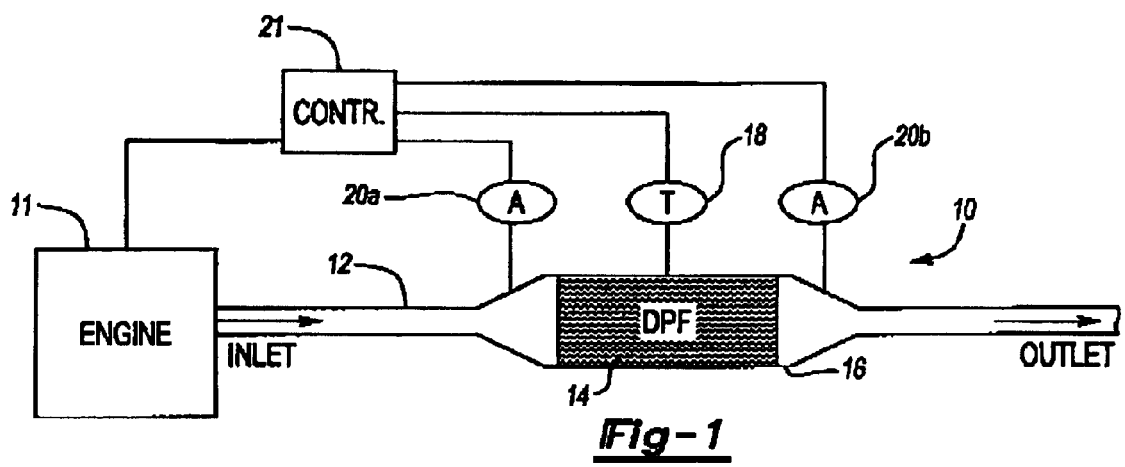
FIG. 1 is a schematic view of the present invention diesel particulate filter monitoring system.

The present invention acoustic filter sensing system is shown at 10 in FIG. 1. System 10 is part of a powertrain system including an engine 11 connected to a portion of an exhaust system 12 having a particulate filter 14 disposed within a portion of the exhaust system 12. The filter 14 is typically constructed from a ceramic honeycomb-shaped material, as is known in the art. In prior art systems, pressure sensors are arranged on either side of the filter 14 to determine the pressure drop across the filter 14, as known in the art. Pressure sensors typically respond to very low frequencies, typically for example up to 10 Hz. Moreover, pressure sensors only measure the absolute magnitude.

A temperature sensor 18 is used to determine the temperature of the filter 14 for determining when to run the regeneration cycle. The present invention also utilizes acoustic sensors 20a and 20b that preferably may be arranged downstream or on either side of the filter 14 to detect acoustic emissions generated within the exhaust system 12 or determine the acoustic transfer function of engine generated sounds through the exhaust system. Unlike pressure sensors, the acoustic sensors 20a and 20b detect frequencies at a much higher level than in pressure measurement, for example in the audible noise range from 100 Hz to 1,000 Hz or more. However, it is to be understood that these ranges are only exemplary. The frequencies sensed do not have to be in the audible range. The acoustic sensor may be a modified pressure sensor with the low pass filter removed to provide the higher frequencies. Although two acoustic sensors are shown, only one sensor or more than two sensors may be used depending upon the particular system. Furthermore, the acoustic sensors may be coupled mechanically or by air to various portions of the exhaust system 12, as will be appreciated from the discussion below.

A controller 21 is electrically connected to the sensors 18, 20a, 20b, engine and any other sensors or systems that may provide relevant information to determining the filter state. Depending upon the state of the filter 14, variations in the acoustic transfer function could appear in engine sounds that pass through the filter 14. The acoustic sensors 20a and 20b enable detection of changes in acoustic transfer function relative to other engine operating parameters and/or detect acoustic emissions generated in the exhaust system 12 to determine the state of the filter. The transfer function can be determined by standard digital signal processing techniques resident in hardware or software of the controller 21 readily available to those of ordinary skill in the art. During operation, the acoustical transfer function is monitored to determine the state of the DPF. Additionally, acoustic emissions of the DPF itself can be correlated to the DPF state and used in addition to or as an alternative to transfer function analysis for simplicity. As the filter is loaded, exhaust velocity goes up resulting in higher frequency exhaust emissions sensed downstream of the filter. Additionally, Doppler shift in frequency components could be used to infer exhaust gas flow velocity which may also be correlated to filter state. The state of the DPF is categorized into several domains, some of which may be: filter is clean (FIG. 4A), filter is loading, filter fully loaded (time for regeneration) (FIG. 4B), filter substrate failed (FIG. 4C), etc.

Figure 2:
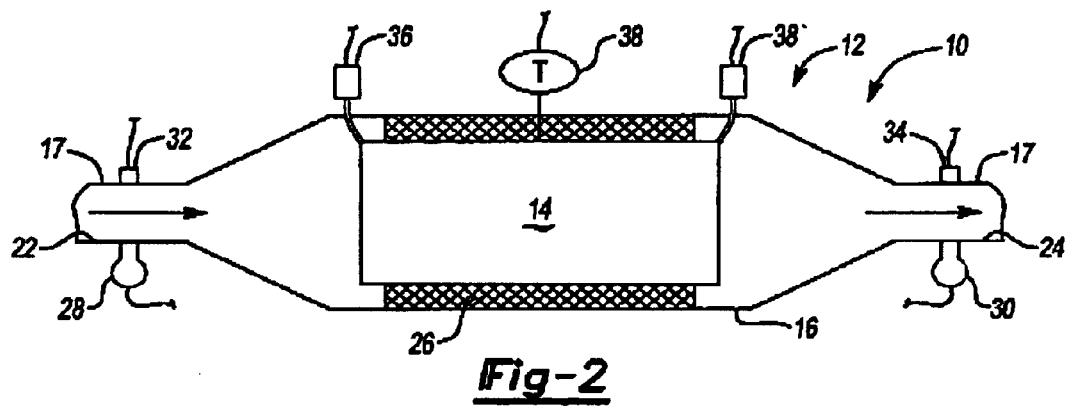
FIG. 2 is a schematic view another diesel particulate filter monitoring system of the present invention.

Referring to FIG. 2, the present invention exhaust system 12 with the present invention acoustic filter sensing system 10 is shown in more detail. The exhaust system 12 includes a can 16 for housing the particulate filter 14. The can 16 includes pipe 17 defining an inlet 22 and outlet 24 on either side of the filter 14. The filter 14 is retained within the can 16 using a material 26, as is well known in the art, to insulate the fragile ceramic filter 14 from vibration against the can 16 while preventing particulate in the exhaust from circumventing the filter 14. As will be appreciated by one of ordinary skilled in the art, the present invention acoustic filter sensing system 10 may incorporate any number of acoustic sensor schemes to measure the acoustic emissions of the diesel particulate filter and/or provide information for determining the acoustical transfer function.

Figure 3:
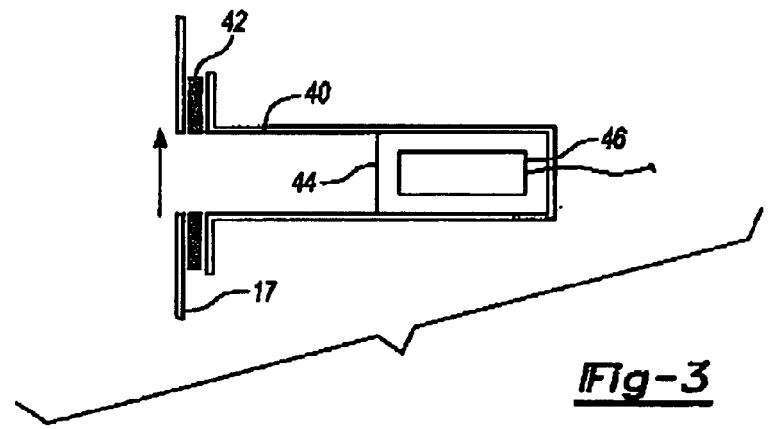
FIG. 3 is an enlarged cross-section of an air coupled acoustic sensor shown in FIG. 2.

The system 10 may include acoustic sensors 28 and 30 fluidly coupled to the exhaust system 12 on either side of the filter 14. By fluidly coupled it is meant that the acoustic sensors 28 and 30 are in fluid communication with the flow of exhaust through the exhaust system 12. As shown in FIG. 3, the fluidly coupled sensors 28 and 30 may include a housing 40 secured to the pipe 17 by any suitable mechanical means. Insulation 42 may be arranged between the housing and the pipe 17 to insulate the acoustic sensor 28 and 30 from the heat. The sensors 28 and 30 may include a diaphragm separating the microphone 46 from the harsh environment of the exhaust gases. The diaphragm 44 may be constructed from of stainless steel, ceramic, or any other suitable material that is resistant to sulfuric acid and other harsh chemicals and/or temperatures that are typically present in exhaust gas.

Referring to FIG. 2, the system 10 may also include sensors 32 and 34 mechanically coupled to the pipe 17 on either side of the filter 14. Sensors 36 and 38 may be mechanically coupled directly to either side of the filter 14. By mechanically coupled, it is meant that the microphone of the mechanical acoustic sensors 32, 34, 36 and 38 are secured to the housing to sense the vibrations in the walls of the exhaust system 12 to take into account the effects structurally borne acoustic vibrations of the exhaust system 12. The acoustic sensors 28–38 determine the acoustical transfer function by comparing the acoustic emissions upstream of the filter 14 with the acoustic emissions downstream of the filter 14. This may be accomplished in any number of ways. For example, the output from fluidly coupled acoustic sensor 30 may be compared to the output of fluidly coupled acoustic sensor 28. Alternatively or additionally, the output from mechanically coupled acoustic sensor 34 may be compared to the output of mechanically coupled of acoustic sensor 32. Similarly, the output of mechanically coupled acoustic sensor 38 may be compared to the output of mechanically coupled acoustic sensor 36, which may compared to the outputs of mechanically coupled acoustic sensor 32 and 34. Moreover, the outputs from the fluidly coupled acoustic sensors 28 and 30 may be compared to the outputs of the mechanically coupled acoustic sensors 32–38, or any other combination thereof.

A model (relationship) between transfer function and/or acoustic DPF emissions and filter state is derived from both physical and empirical measurements. Referring to FIG. 5, a simplified block diagram of the present invention method is shown. The relationship of the acoustical transfer function and filter state, is modeled as depicted in block 60. Similar relationships are determined for acoustic DPF emissions as well. The gas flow rate 62 may be determined by calculating the volumetric output of the engine utilizing mass flow sensors, the engine speed, fuel flow rates, and other engine operating characteristics. The controller 21 receives and processes the information from the sensors and vehicle systems to determine the filter state. The acoustic transfer function is dependent upon the gas flow rate 62 and/or the state of the filter 66. For example, as shown in FIG. 4A, the acoustic emission is shown for a clean filter. As the filter becomes full, higher frequencies are more favorably passed through the acoustic sensor, as shown in FIG. 4B. For a failed filter in which there has been a bum through or a hole in the filter, a greater range of frequencies may pass through the filter as shown in FIG. 4C. The graph shown in FIGS. 4A–4C are intended only to illustrate the invention, and the actual frequency response and amplitude for a particular filter may be different than that shown. Once the relationship has been modeled as a transfer function 64, the condition of the filter may be monitored by the acoustic sensors 20a and 20b as shown at block 68. The sensed conditions may be compared to data stored by an engine or exhaust controller to determine the domain or the state of the filter as indicated at block 40.

When the filter is near full loading, the engine/exhaust control system can schedule a regeneration cycle. When the filter substrate is detected as failed, the engine/exhaust controller can signal the driver of a need for service.

In operation, the exhaust tract will be a reverberant system with sounds such as those generated by the engine reflecting up and down the exhaust tract. As a result, the sound measurement at any point in the exhaust system will be a function of present and past sounds injected into the system, i.e., $$y(t) = \int_0^{t_d} g(t')x(t-t')\,dt' + \int_0^{t_o} f(t')y(t-t')\,dt', \quad \text{(Equation 1)}$$

where y(t) is the instantaneous sound level measured at a given microphone input, x(t) is the sound input from the engine, $t_d$ is a characteristic delay and $t_o$ is a time selected to be long enough to cover significant contributions from exhaust tract acoustic reverberations.

The integrals are readily recognized as time domain convolutions, which result in frequency domain multiplications, i.e., $$Y(w)=G(w)X(w)+F(w)Y(w), \quad \text{(Equation 2)}$$

where w is frequency and X, G, Y and F are the Fourier transforms of x, g, y and f respectively. Solving for Y(w) it is seen that:

$$Y(w) = \frac{G(w)X(w)}{1-F(w)}, \quad \text{(Equation 3)}$$

where the transfer function T(w) is given by:

$$T(w) = \frac{G(w)}{1 - F(w)},$$ (Equation 4)

which gives:

Y(w)=T(w)X(w), (Equation 5)

If x(t) is measured upstream of the DPF filter and y(t) is measured downstream of the DPF in a two sensor approach, T(w) can be determined as:

$$T(w) = \frac{Y(w)}{X(w)}$$ (Equation 6)

where x(t) in this case provides an estimate of the engine induced noise. In the case of an acoustic tract such as an exhaust system, T(w) will be influenced by temperature (which effects the speed of sound), exhaust tract geometry and gas flow characteristics. By monitoring temperature using temperature sensor 18 or inferred temperature from other sensor signals, and/or gas flow characteristics in conjunction with T(w), the dependence of T(w) on these parameters may be determined. In some cases it may even be possible to construct analytic parametric models (physical or empirical) to quantify this dependence. In other cases the dependence can be stored as look up tables.

Once temperature and/or gas flow have been accounted for, the remaining characteristics of T(w) can be expected to depend heavily on the materials and geometry of the exhaust tract. Assuming that the other components of an exhaust tract (muffler, resonator, catalyst, etc.) are stable on the time scale in which a DPF loads with soot, any variation in T(w) not accounted for by temperature and/or gas flow characteristics may be attributed in part to changes in the DPF. By correlating these changes to the degree of soot loading in the DPF or other conditions of interest such as cracking, changes in measured T(w) may then be used to infer the degree of soot loading and/or condition in the DPF.

In some cases it may be necessary to account for variations in acoustic response between different types of soot. In such cases, soot production models for the engine used in conjunction with the DPF may be developed to increase the fidelity of the model for T(w) with respect to its variation relating to soot loading or other conditions of interest in the DPF.

In some cases, if the temperature variation along the exhaust tract is varying slowly enough and a suitable parametric model for T(w) may be developed, preferably physically based, least squares fitting techniques may be used to estimate a model for T(w). In such an approach parametric equations are selected, preferably physically based, for g and f that can be reasonably fit to the measured data. The functional form of these equations will vary between exhaust tract configurations and may be constructed from first principles using acoustic analysis and/or inspection of empirical results in standard system identification approaches.

Assume that g(t) may be described as an equation with n parameters a1, a2, a3 ... an and f(t) can be described as an equation with m parameters b1, b2 ... bm, i.e., g(t')→g(t',a1,a2 ... an), (Equation 7)

f(t')→g(t',b1,b2 ... bm), (Equation 8)

where the form of these equations is obtained from physical modeling from acoustic analysis and/or empirical system identification techniques. Further, assuming the instantaneous sound amplitude y(t) is measured continuously at a point downstream of the DPF filter and x(t) is the instantaneous sound amplitude measured at a point upstream of the filter, applying the general expressions for g and f, the following relationship is obtained.

$$y_p(t) = \int_0^{\tau_d} g(t', b1, b2 \ldots bm)x(t-t')dt' + \int_0^{\tau_0} f(t', a1, a2 \ldots an)y(t-t')dt',$$ (Equation 9)

where $y_p(t)$ is a predicted value for the measured quantity y(t). By comparing the predicted and measured values a squared error can be constructed as follows:

$$e(t)=[y_p(t)-y(t)]$$ (Equation 10)

$$E(t) = \int^{t_f} e(t-t') * dt$$ (Equation 11)

where e(t) is the instantaneous error and E(t) is the integrated error over a time interval $t_f$ selected to be long enough to have a slowly varying value for E(t), but still short enough to have approximately constant temperature and DPF soot loading throughout the time interval.

Optimal values for the parameters a1 ... an and b1 ... bm are then obtained by setting the variation in error with respect to the various parameters equal to zero and solving the resulting n+m equations for the parameters, i.e., $$\frac{\partial E(t)}{\partial a1} = 2[y_p(t) - y(t)]\frac{\partial y_p(t)}{\partial a1} = 2[y_p(t) - y(t)]$$ (Equation 12)

$$\int_0^{\tau_0} \frac{\partial}{\partial a1} f(t', a1, a2 \ldots an)y(t-t')dt' = 0$$

$$\frac{\partial E(t)}{\partial a2} = 2[y_p(t) - y(t)]\frac{\partial y_p(t)}{\partial a2} = 2[y_p(t) - y(t)]$$

$$\int_0^{\tau_0} \frac{\partial}{\partial a2} f(t', a1, a2 \ldots an)y(t-t')dt' = 0$$

⋮

$$\frac{\partial E(t)}{\partial an} = 2[y_p(t) - y(t)]\frac{\partial y_p(t)}{\partial an} = 2[y_p(t) - y(t)]$$

$$\int_0^{\tau_0} \frac{\partial}{\partial an} f(t', a1, a2 \ldots an)y(t-t')dt' = 0$$

$$\frac{\partial E(t)}{\partial b1} = 2[y_p(t) - y(t)]\frac{\partial y_p(t)}{\partial b1} = 2[y_p(t) - y(t)]$$

$$\int_0^{\tau_d} \frac{\partial}{\partial b1} g(t', b1, b2 \ldots bm)x(t-t')dt' = 0$$

$$\frac{\partial E(t)}{\partial b2} = 2[y_p(t) - y(t)]\frac{\partial y_p(t)}{\partial b2} = 2[y_p(t) - y(t)]$$

$$\int_0^{\tau_d} \frac{\partial}{\partial b2} g(t', b1, b2 \ldots bm)x(t-t')dt' = 0$$

⋮

$$\frac{\partial E(t)}{\partial bm} = 2[y_p(t) - y(t)]\frac{\partial y_p(t)}{\partial bm} = 2[y_p(t) - y(t)]$$

$$\int_0^{\tau_d} \frac{\partial}{\partial bm} g(t', b1, b2 \ldots bm)x(t-t')dt' = 0$$

Depending on the functional forms selected for f(t) and g(t), these equations may or may not be analytically integrable and may or may not be analytically solvable with respect to the parameters a1 ... an and b1 ... bn. However, many techniques are described in the literature, which are well known to those of ordinary skill in the art, for methods to do numerical integrations and obtain numerical solutions to systems of equations that cannot be readily solved by algebraic techniques. Many of these solution techniques are found in the general area of "system identification." Additionally, for certain choices of functional forms for g(t',a1,a2 . . . an) and f(t',b1,b2 . . . bn), it is possible to extract estimates of the a and/or b parameters with only a y(t) or x(t) measurement, i.e. only a single acoustic sensor located upstream or downstream of the DPF. This has advantages in both hardware and installation costs.

In a preferred embodiment of the invention, correlations are made between the transfer function T(w) as determined from Equation 6 and the degree of soot loading and/or condition of the DPF. T(w) is determined continuously or at pre-selected intervals and the correlations are used to provide an estimate of soot loading and/or condition of the DPF where the "condition" includes predetermined states of interest, such as cracks or over temperature excursions to be used for service or OBD diagnostic purposes.

In a second preferred embodiment, correlations are made between the parameter values of the modeling functions g(t',a1,a2 . . . an) and f(t',b1,b2 . . . bn) and the degree of soot loading and/or condition of the DPF. The parameters are continuously or periodically updated by solving the n+m system of Equations 12. The correlations are used to provide an estimate of soot loading and/or condition of the DPF where the "condition" includes predetermined states of interest, such as cracks in the DPF or over temperature during regeneration to be used for service or OBD diagnostic purposes.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

We claim:

1. A particulate filter system comprising:
   an exhaust system;
   a filter disposed in said exhaust system; and
   an acoustic sensor detecting a frequency relating to said filter, said frequency corresponding to a filter state, wherein said acoustic sensor is a first acoustic sensor having a diaphragm and is fluidly coupled to a portion of said exhaust system, with a fluid within said exhaust system and in communication with said filter acting on said diaphragm to produce said frequency.

2. The system according to claim 1, wherein a second acoustic sensor is mechanically coupled to a portion of said exhaust system for detecting a vibration of said exhaust system, and a controller adjusting an output relating to said frequency for the effects of said vibration.

3. A particulate filter system comprising:
   an exhaust system;
   a filter disposed in said exhaust system;
   an acoustic sensor detecting a frequency relating to said filter, said frequency corresponding to a filter state; and
   a controller communicating with said acoustic sensor and obtaining a transfer function from said frequency.

4. The system according to claim 3, wherein a temperature sensor communicates with said controller for detecting a temperature of an exhaust gas in said exhaust system.

5. The system according to claim 3, wherein said controller determines a gas flow through said filter.

6. A particulate filter system comprising:
   an exhaust system;
   a filter disposed in said exhaust system;
   a first acoustic sensor arranged on a first side of said filter and a second acoustic sensor arranged on a second side of said filter, at least one of said first and second acoustic sensors detecting a frequency relating to said filter, said frequency corresponding to a filter state; and
   a controller communicating with said first and second acoustic sensors, and said controller comparing a first and second output respectively associated with said first and second acoustic sensors to determine said filter state.

7. The system according to claim 6, wherein said controller calculates a delay characteristic of said exhaust system, said frequency adjusted for said delay.

8. The system according to claim 1, wherein said acoustic sensor detects frequencies above approximately 10 Hz.

9. The system according to claim 8, wherein said acoustic sensor detects frequencies in a range including from approximately 100 Hz to 1000 Hz.

10. The system according to claim 1, wherein insulation is arranged between said exhaust system and said acoustic sensor.

11. A method of determining a filter state of a particulate filter system comprising the steps of:
   a) detecting a frequency with a sensor;
   b) monitoring a powertrain system parameter;
   c) processing the frequency from the sensor relative to the powertrain system parameter to obtain a filter information; and
   d) comparing the filter information to a known filter state to determine a present filter state.

12. A method of determining a filter state of a particulate filter system comprising the steps of:
   a) detecting a frequency with a sensor;
   b) monitoring a powertrain system parameter;
   c) processing the frequency from the sensor relative to the powertrain system parameter to obtain a filter information including determining an acoustical transfer function for the frequency; and
   d) comparing the filter information to a known filter state to determine a present filter state.

13. The method according to claim 12, wherein step c) includes determining a time delay for an exhaust system.

14. The method according to claim 11, wherein step c) includes determining an acoustical emission from the filter.

15. The system according to claim 6, wherein said first and second sides correspond to inlet and outlet sides of said filter.

* * * * *